US008280472B2

(12) United States Patent
Li et al.

(10) Patent No.: US 8,280,472 B2
(45) Date of Patent: Oct. 2, 2012

(54) METHOD AND APPARATUS FOR MEASURING BLOOD OXYGEN SATURATION

(75) Inventors: Xu Li, Shenzhen (CN); Xu Zhang, Shenzhen (CN)

(73) Assignee: Shenzhen Mindray Bio-Medical Electronics Co., Ltd., Sehnzhen (CN)

( * ) Notice: Subject to any disclaimer, the term of this patent is extended or adjusted under 35 U.S.C. 154(b) by 1313 days.

(21) Appl. No.: 11/965,634

(22) Filed: Dec. 27, 2007

(65) Prior Publication Data
US 2009/0024012 A1 Jan. 22, 2009

(30) Foreign Application Priority Data
Jul. 19, 2007 (CN) .......................... 2007 1 0075900

(51) Int. Cl.
*A61B 5/1455* (2006.01)
(52) U.S. Cl. ........................................ 600/323; 600/310
(58) Field of Classification Search ........... 600/309–344
See application file for complete search history.

(56) References Cited

U.S. PATENT DOCUMENTS

| 4,807,631 | A | * | 2/1989 | Hersh et al. | 600/323 |
|---|---|---|---|---|---|
| 5,213,099 | A | * | 5/1993 | Tripp, Jr. | 600/324 |
| 5,598,841 | A | * | 2/1997 | Taniji et al. | 600/342 |
| 6,128,525 | A | * | 10/2000 | Zeng et al. | 600/476 |
| 6,556,853 | B1 | * | 4/2003 | Cabib et al. | 600/407 |
| 2005/0192488 | A1 | | 9/2005 | Bryenton et al. | |
| 2006/0206019 | A1 | * | 9/2006 | Zhang et al. | 600/323 |
| 2007/0149872 | A1 | * | 6/2007 | Zhang et al. | 600/336 |

FOREIGN PATENT DOCUMENTS

| CN | 1104475 | 7/1995 |
|---|---|---|
| CN | 1600271 | 3/2005 |
| WO | WO2006092050 | 9/2006 |

OTHER PUBLICATIONS

Lin Zhengjian, "Three wave length blood oxygen degree of saturation measuring instrument's development," Master Dissertation, University of Electronic Science and Technology of China, pp. 9-11, Dec. 31, 2005.

* cited by examiner

*Primary Examiner* — Eric Winakur
*Assistant Examiner* — Marjan Fardanesh
(74) *Attorney, Agent, or Firm* — Kory D. Christensen; Stoel Rives LLP

(57) ABSTRACT

A method and apparatus are disclosed for measuring blood oxygen saturation by using spectrophotometry to improve the accuracy of the measurement under a condition of low perfusion.

22 Claims, 6 Drawing Sheets

METHOD AND APPARATUS FOR MEASURING BLOOD OXYGEN SATURATION

RELATED APPLICATIONS

This application claims priority to Chinese Patent Application No. 200710075900.2, filed Jul. 19, 2007, which is hereby incorporated by reference in its entirety.

TECHNICAL FIELD

This disclosure relates to a method and apparatus for measuring blood oxygen saturation.

SUMMARY

The embodiments disclosed herein provide a method and apparatus for measuring blood oxygen saturation by using spectrophotometry to improve the accuracy of the measurement under a condition of low perfusion.

DETAILED DESCRIPTION OF PREFERRED EMBODIMENTS

Figure 1:
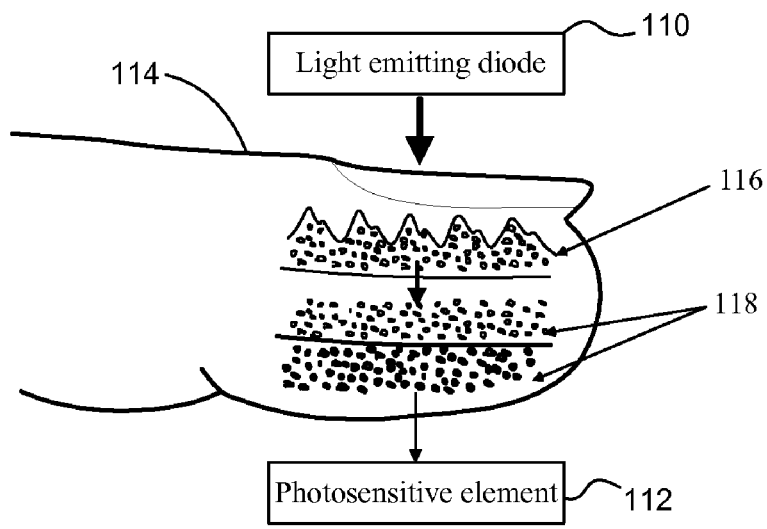
FIG. 1 is a schematic diagram of tissues absorbing lights.

Currently, blood oxygen saturation is commonly measured by using a pulse oximeter. The basic structure of the measuring apparatus includes a blood oxygen probe and a signal processing apparatus. As shown in FIG. 1, the blood oxygen probe is a sensor consisting of a light-emitting diode 110 and a photosensitive element 112. The light-emitting diode 110 provides lights having two and more kinds of wavelengths. The function of the photosensitive element 112 is to convert a light signal through the tissue periphery and having information on the blood oxygen saturation into an electrical signal, which is then digitalized via a signal processing circuit. With this digital signal, the blood oxygen saturation is calculated by using a specific signal processing algorithm.

The measurement of the blood oxygen saturation by the pulse oximeter is based on spectrophotometry, which measures the blood oxygen saturation by using the pulsation of arterial blood within the human tissue periphery caused by pulse waves. Spectrophotometry includes transmitted light and reflected light, both on the basis of the Lambert-Beer law and light scattering theory. Oxyhemoglobin ($HbO_2$) and deoxyhemoglobin (Hb) have different optical properties in the red light spectrum and the infrared light spectrum and have different optical absorption coefficients, thus influencing the transmittance of the red light and the infrared light through a finger 114. When the red and infrared lights with a certain light intensity are applied to the finger 114 and the transmitted light intensities of the two lights are then detected respectively, the concentration of $HbO_2$ is calculated by the ratio of the variations of the optical densities of the two lights for the finger 114, thus calculating the blood oxygen saturation.

In engineering, the red light of approximately 660 nm and the infrared light of approximately 940 nm are respectively irradiated to measure tissues of the human body, as illustrated in FIG. 1, in which the reference sign 116 indicates the composition of pulsatile arterial blood and the reference sign 118 indicates the composition of nonpulsatile arterial blood and the static composition of non-moving tissue.

Figure 2:
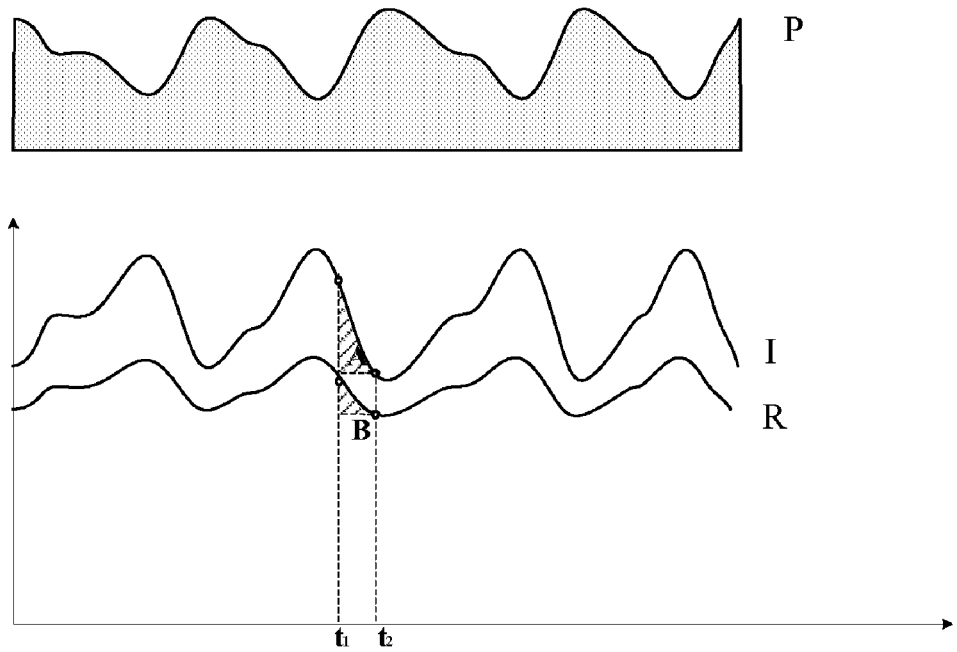
FIG. 2 is a schematic diagram of signals corresponding to lights transmitted through the tissues shown in FIG. 1.

In FIG. 2, waveform P represents a regular change of human blood as a heart beats, and waveforms R and I represent the current signals ($i_R$ and $i_I$, respectively) corresponding to the transmitted lights respectively irradiated by the red light and the infrared light. The greater the blood volume in the measured tissue, the lower the intensities of the transmitted lights. Therefore, the waveform P is reversed with $i_R$ or $i_I$. The pulse blood oxygen saturation may be calculated from two points in the respective waveform corresponding to t1, t2:

$$SpO_2 = (A \times R + B)/(C \times R + D), \qquad (1)$$

where:
$A = \epsilon_4$;
$B = -\epsilon_2$;
$C = \epsilon_4 - \epsilon_3$;
$D = \epsilon_1 - \epsilon_2$;
$\epsilon_1, \epsilon_2$ are respectively the absorption rates of $HbO_2$ and Hb to the red light of approximately 660 nm; and
$\epsilon_3, \epsilon_4$ are respectively the absorption rates of $HbO_2$ and Hb to the infrared light of approximately 940 nm.

Research shows that the pulse blood oxygen saturation is approximate to the arterial blood oxygen saturation ($SaO_2$):

$$R = \frac{\ln i_I(a)/i_I(b)}{\ln i_R(a)/i_R(b)} = \frac{\ln i_I(a) - \ln i_I(b)}{\ln i_R(a) - \ln i_R(b)} \qquad (2)$$

$$R = \frac{\ln i_I(a)/i_I(b)}{\ln i_R(a)/i_R(b)} = \frac{\ln i_I(a) - \ln i_I(b)}{\ln i_R(a) - \ln i_R(b)},$$

where:

R corresponds to the blood oxygen saturation in a one-to-one manner, that is, the pulse blood oxygen saturation is derived from the variation of the two lights irradiating through human tissues. To reduce the effect of signal interference, a and b usually take values at the crest and the valley of the wave within a pulse cycle. Here, the formula for R is as follows:

$$\frac{\ln i_I(a)/i_I(b)}{\ln i_R(a)/i_R(b)} = \frac{\ln i_{Im}/i_{IM}}{\ln i_{Rm}/i_{RM}} = \frac{\ln i_{Im} - i_{IM}}{\ln i_{Rm} - i_{RM}} = R, \qquad (3)$$

where:

$i_{RM}$ is the maximum transmitted light of the red light, $i_{Rm}$ is the minimum transmitted light of the red light, $I_{IM}$ is the maximum transmitted light of the infrared light, and $I_{Im}$ is the minimum transmitted light of the infrared light.

For the red light:

$$\ln i_{Rm}/i_{RM} = \ln\left(1 - \frac{i_{RM} - i_{Rm}}{i_{RM}}\right). \quad (4)$$

When the ratio of the pulse component to the direct current component, that is, $(i_{RM}-i_{Rm})/i_{RM}$, is lower, $$\ln\left(1 - \frac{i_{RM} - i_{Rm}}{i_{RM}}\right) \approx \frac{i_{RM} - i_{Rm}}{i_{RM}}$$

$\approx$ the ratio of the pulse component to the direct current component

Accordingly, R may be written as follows:

$$R = \frac{Red_{AC}/Red_{DC}}{Ir_{AC}/Ir_{DC}}. \quad (5)$$

The above formulas are the common methods for calculating the blood oxygen saturation. It may be derived from the above formulas in that only the blood oxygen content R in formula (1) is variable when the light-emitting diode 110 is given. The direct current components of the red light and the infrared light are still stable during a period of time, while the alternative current components of the two lights are the main factors influencing R. Therefore, there is a defect in this method in that when a patient is under the condition of low perfusion, the signal-to-noise ratio is very low because the amount of variation is very weak. There are serious distortions in the wave peaks and the wave valleys at that time due to superimposed noise.

Figure 3:
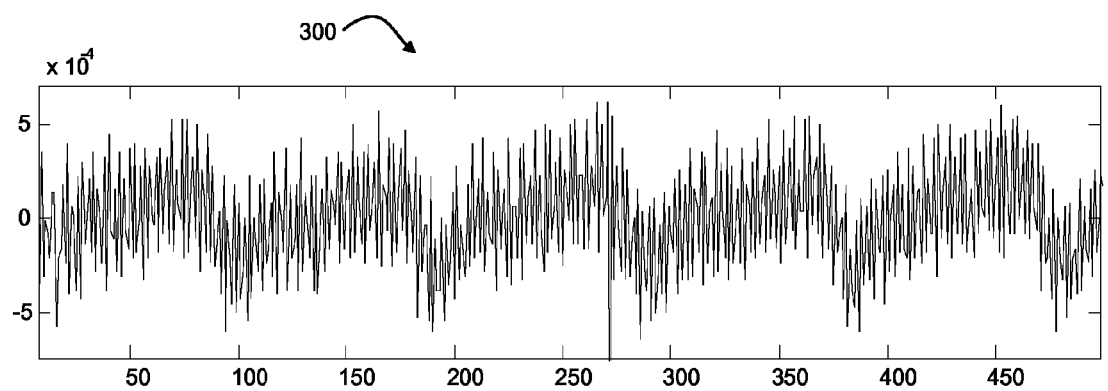
FIG. 3 is a schematic diagram of an original sampling signal.
Figure 4:
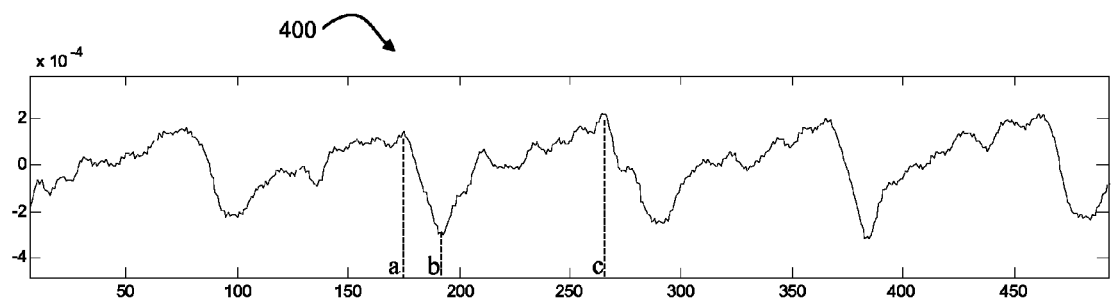
FIG. 4 is a schematic diagram of the signal shown in FIG. 3 filtered through a low-pass filter.

FIG. 3 is a section of plethysmogram 300 under the condition of low perfusion. Since a human's pulse is generally fewer than 300 times per minute (corresponding frequency is 5 Hz), a signal is passed through a finite impulse response (FIR) filter with a cutoff frequency of approximately 6 Hz to filter most of the noise beyond the signal bandwidth. The filtered signal 400 is illustrated in FIG. 4. Because interference exists, it is hard to accurately determine the wave peaks and the wave valleys of the two lights, and thus error will exist in finding the wave peaks and the wave valleys of the pulse wave. The wave peaks and the wave valleys of the signals in the figure are $M_I$, $M_R$, $V_I$, and $V_R$, respectively (e.g., see FIG. 7). The measured ratio of alternating current to direct current is also possibly false due to the distortion of the wave peaks and the wave valleys. At this time, it is hard to ensure that the measurements of the blood oxygen saturation are correct.

In one embodiment, a method for measuring blood oxygen saturation includes acquiring intensities of transmitted lights that are obtained by transmitting respectively a light of a first wavelength and a light of a second wavelength through organism tissues, and converting the intensities of the transmitted lights into corresponding signals for the light of the first wavelength and the light of the second wavelength. The method further includes defining at least one interval on waveforms of the signals for the light of the first wavelength and the light of the second wavelength, and performing an area integral on the waveforms of the signals for the light of the first wavelength and the light of the second wavelength in the at least one interval to produce a total area integral of the signal for the light of the first wavelength and a total area integral of the signal for the light of the second wavelength. The method also includes calculating a ratio of the total area integral of the signal for the light of the first wavelength to the total area integral of the signal for the light of the second wavelength as a blood oxygen content R, and calculating a blood oxygen saturation according to the following formula:

$$SpO_2 = (A \times R + B)/(C \times R + D),$$

where $SpO_2$ is the blood oxygen saturation;
$A = \epsilon_4$;
$B = -\epsilon_2$;
$C = \epsilon_4 - \epsilon_3$;
$D = \epsilon_1 - \epsilon_2$;
$\epsilon_1$, $\epsilon_2$ are respectively an absorption rate of oxyhemoglobin to the light of the first wavelength and an absorption rate of deoxyhemoglobin to the light of the first wavelength, and
$\epsilon_3$, $\epsilon_4$ are respectively an absorption rate of oxyhemoglobin to the light of the second wavelength and an absorption rate of deoxyhemoglobin to the light of the second wavelength.

In certain such embodiments, the method further includes, before defining the at least one interval, performing respectively a natural logarithm operation on the signal for the light of the first wavelength and the signal for the light of the second wavelength.

In addition, or in other embodiments, the at least one interval is divided into different confidence intervals according to different degrees of noise interference in a pulse fluctuation cycle. A confidence value of one interval with relatively high interference is less than that of another confidence interval with relatively low interference. The total area integral of the signal for the light of the first wavelength includes a sum of the products of the area integral of the waveform of the signal for the light of the first wavelength in all the confidence intervals and the corresponding confidence, and the total area integral of the signal for the light of the second wavelength is the sum of the products of the area integral of the waveform of the signal for the light of the second wavelength in all the confidence intervals and the corresponding confidence.

The confidence intervals may include a rise stage interval in which the signal for the light of the first wavelength and the signal for the light of the second wavelength are at a rise edge. The confidence intervals may also include a fall edge interval in which the signal for the light of the first wavelength and the signal for the light of the second wavelength are at a fall edge. The confidence of the rise edge interval may be less than the confidence of the fall edge interval.

In certain embodiments, determination of the rise edge intervals and the fall edge intervals includes searching the wave valley in each pulse cycle of the signal for the light of the first wavelength and the wave valley in each pulse cycle of the signal for the light of the second wavelength from the signal over a period of time to obtain positions $V_{R1}, V_{R2}, V_{Rj} \ldots V_{Rn}$ of the wave valleys of the signal for the light of the first wavelength and positions $V_{I1}, V_{I2}, V_{Ij} \ldots V_{In}$ of the wave valleys of the signal for the light of the second wavelength, where j is the j-th pulse cycle. The method also includes determining positions $M_{R1}, M_{R2}, M_{Rj} \ldots M_{Rn}$ of the wave peaks of the signal for the light of the first wavelength and positions $M_{I1}, M_{I2}, M_{Ij} \ldots M_{In}$ of the wave peaks of the signal for the light of the second wavelength based on the positions of the wave valleys. The method further includes determining, based on the values of the wave peak and the wave valley of each pulse cycle, a length L of the fall edge of the pulse cycle, $$L = \min(V_{Ri}, V_{Ii}) - \max(M_{Ri}, M_{Ii}),$$

where $V_{Ri}$, $M_{Ri}$ are respectively positions of the wave peak and the wave valley in the i-th pulse cycle of the signal for the light of the first wavelength, $V_{Ii}$, $M_{Ii}$ are respectively positions of the wave peak and the wave valley in the i-th pulse cycle of the signal for the light of the second wavelength, and i is any value between 1 and n.

The method also includes determining the rise interval $[V_{ri}, M_{ri}]$ and the fall interval $[M_{fi}, V_{fi}]$ in the i-th pulse cycle based on the values of the wave peak and the wave valley and the length L of the fall edge in the i-th pulse cycle, wherein $V_{ri}=\max(V_{R(i-1)}, V_{I(i-1)})$, $M_{ri}=\min(M_{Ri}, M_{Ii})$, $M_{fi}=\max(M_{Ri}, M_{Ii})+L\times 0.1$, and $V_{fi}=\min(V_{Ri}, V_{Ii})-L\times 0.1$.

In determining the length L of the fall edge, when $\min(V_{Ri}, V_{Ii}) <= \max(M_{Ri}, M_{Ii})$, the corresponding time calculation of the blood oxygen may be cancelled, and when $\min(V_{Ri}, V_{Ii}) > \max(M_{Ri}, M_{Ii})$, the length L of the fall edge may be determined as:

$$L=\min(V_{Ri}, V_{Ii})-\max(M_{Ri}, M_{Ii}).$$

In certain embodiments, the confidence of the rise interval edge is $\sigma_r$, and the confidence of the fall edge interval is $\sigma_f$, wherein $$\sigma_r = 0.25 \times (0.8 - \gamma_{v-1} - \gamma_m),$$

$$\sigma_f = 0.8 - \gamma_v - \gamma_m,$$

where $\gamma_m$ is a fluctuation coefficient of the wave peak in the i-th pulse cycle and $\gamma_v$ is a fluctuation coefficient of the wave valley in the i-th pulse cycle, $$\gamma_m = \frac{|M_{Ri} - M_{Ii}|}{L}$$

$$\gamma_v = \frac{|V_{Ri} - V_{Ii}|}{L}.$$

In addition, or in other embodiments, the blood oxygen content of the i-th pulse cycle is:

$$R_i = \frac{\sigma_r \cdot R_{ri} + \sigma_f \cdot R_{fi}}{\sigma_r + \sigma_f}.$$

When the fluctuation coefficient of the wave peak or the wave valley is more than approximately 0.4, the confidence of the blood oxygen content in the corresponding pulse cycle may be zero.

In one embodiment, an apparatus for measuring blood oxygen saturation includes a signal generation component to acquire intensities of the transmitted lights that are obtained by transmitting a light of a first wavelength and a light of a second wavelength through organism tissues and to convert the acquired intensities of the transmitted lights into corresponding signals for the light of the first wavelength and the light of the second wavelength. The apparatus also includes an interval determination component to define at least one interval on waveforms of the signals for the light of the first wavelength and the light of the second wavelength, and an integral component to perform a natural logarithm operation on the signals for the light of the first wavelength and the light of the second wavelength in the at least one interval respectively. The apparatus also includes a first calculating component and a second calculating component. The first calculating component is to calculate a ratio of the total area integral of the signal for the light of first wavelength to the total area integral of the signal for the light of the second wavelength as the blood oxygen content R. The second calculating component is to calculate blood oxygen saturation according to the following formula:

$$SpO_2 = (A \times R + B)/(C \times R + D),$$

where $SpO_2$ is the blood oxygen saturation;

$A = \epsilon_4$;
$B = -\epsilon_2$;
$C = \epsilon_4 - \epsilon_3$;
$D = \epsilon_1 - \epsilon_2$;

$\epsilon_1, \epsilon_2$ are respectively an absorption rate of oxyhemoglobin to the red light and an absorption rate of deoxyhemoglobin to the red light; and $\epsilon_3, \epsilon_3$ are respectively an absorption rate of oxyhemoglobin to the infrared light and an absorption rate of deoxyhemoglobin to the infrared light.

In certain embodiments, the apparatus also includes a logarithm operation component to perform a natural logarithm operation on the signals for the light of the first wavelength and the light of the second wavelength respectively and to output the result to the integral component.

The interval determination component may be used to divide the at least one interval into different confidence intervals according to the different degrees of the noise interference within the pulse fluctuation cycle. The confidence for the interval with greater interference is less than the confidence for the interval with lower interference. The integral component may be further used to calculate the total area integral of the signal for the light of the first wavelength and the total area integral of the signal for the light of the second wavelength according to the confidence of each confidence interval.

The confidence intervals may include a rise edge interval in which the signal for the light of the first wavelength and the signal for the light of the second wavelength are at a rise stage and a fall edge interval in which the signal for the light of the first wavelength and the signal for the light of the second wavelength are at a fall stage. The confidence of the rise edge interval in certain embodiments is less than the confidence of the fall edge interval.

In certain embodiments the interval determination module may include a peak and valley determination unit for respectively searching a wave valley in each pulse cycle of the signal for the light of the first wavelength and a wave valley in each pulse cycle of the signal for the light of the second wavelength from the signal over a period of time to obtain positions $V_{R1}, V_{R2}, V_{Rj} \ldots V_{Rn}$ of the wave valleys of the signal for the light of the first wavelength and positions $V_{I1}, V_{I2}, V_{Ij} \ldots V_{In}$ of the wave valleys of the signal for the light of the second wavelength, where j is the j-th pulse cycle. The peak and valley determination unit may also determine positions $M_{R1}, M_{R2}, M_{Rj} \ldots M_{Rn}$ of the wave peaks of the signal for the light of the first wavelength and positions $M_{I1}, M_{I2}, M_{Ij} \ldots M_{In}$ of the wave peaks of the signal for the light of the second wavelength based on the positions of the wave valleys;

In certain embodiments the interval determination module may also include a fall edge length determination unit to determine, based on the values of the wave peak and the wave valley of each pulse cycle, length L of the fall edge of the pulse cycle, $$L=\min(V_{Ri}, V_{Ii})-\max(M_{Ri}, M_{Ii}),$$

where $V_{Ri}, M_{Ri}$ are respectively positions of the wave peak and the wave valley in the i-th pulse cycle of the signal for the light of the first wavelength, $V_{Ii}, M_{Ii}$ are respectively positions of the wave peak and the wave valley in the i-th pulse cycle of the signal for the light of the second wavelength, and i is any value between 1 and n.

In certain embodiments the interval determination module may also include a rise edge and fall edge intervals determination unit to determine the rise interval and the fall interval in the i-th pulse cycle based on the values of the wave peak and the wave valley and the length L of the fall edge in the i-th pulse cycle. The rise edge interval is $[V_{ri}, M_{ri}]$ and the fall edge interval is $[M_{fi}, V_{fi}]$, wherein $V_{ri}=\max(V_{R(i-1)}, V_{I(i-1)})$, $M_{ri}=\min(M_{Ri}, M_{Ii})$, $M_{fi}=\max(M_{Ri}, M_{Ii})+L\times 0.1$, and $V_{fi}=\min(V_{Ri}, V_{Ii})-L\times 0.1$.

The interval determination component may further include a confidence determination unit to determine confidences of the rise edge interval and the fall edge interval. The confidence of the rise edge interval is $\sigma_r$, the confidence of the fall edge interval is $\sigma_f$, and $\sigma_r=0.25\times(0.8-\gamma_{v-1}\gamma_m)$, $\sigma_f=0.8-\gamma_v-\gamma_m$, where $\gamma_m$ is the fluctuation coefficient of the wave peak in the i-th pulse cycle and $\gamma_v$ is the fluctuation coefficient of the wave valley at the i-th pulse cycle, $$\gamma_m = \frac{|M_{Ri} - M_{Ii}|}{L}$$

$$\gamma_v = \frac{|V_{Ri} - V_{Ii}|}{L}.$$

In one embodiment, a system for measuring blood oxygen saturation includes means for acquiring intensities of a first light at a first wavelength and a second light at a second wavelength transmitted through organism tissues and for converting the acquired intensities of the transmitted lights into signals corresponding to the light of the first wavelength and the light of the second wavelength. The system also includes means for defining at least one interval on waveforms of the signals for the light of the first wavelength and the light of the second wavelength, and means for performing a natural logarithm operation on the signals for the light of the first wavelength and the light of the second wavelength in the at least one interval. The system also includes first calculating means and second calculating means. The first calculating means is for calculating a ratio of the total area integral of the signal for the light of the first wavelength to the total area integral of the signal for the light of the second wavelength as the blood oxygen content R. The second calculating means is for calculating blood oxygen saturation according to the following formula:

$SpO_2=(A\times R+B)/(C\times R+D)$, where $SpO_2$ is the blood oxygen saturation;
A=$\epsilon_4$;
B=$-\epsilon_2$;
C=$\epsilon_4-\epsilon_3$;
D=$\epsilon_1-\epsilon_2$;
$\epsilon_1, \epsilon_2$ are respectively an absorption rate of oxyhemoglobin to the red light and an absorption rate of deoxyhemoglobin to the red light; and
$\epsilon_3, \epsilon_4$ are respectively an absorption rate of oxyhemoglobin to the infrared light and an absorption rate of deoxyhemoglobin to the infrared light.

The disclosed embodiments provide a method for performing a subsection integral on a pulse wave to eliminate noise, and adopts an area integral on a pulse wave signal instead of the conventional method of extremum ratio. Performing the integral calculation on the waveform of a pulse wave within a period of time may eliminate the influence from white noise and non-white noise in the pulse wave, and it is proved that the result of the integral calculation is equal to the AC component of the pulse wave. Thus, the blood oxygen saturation is calculated by using the result of the integral calculation. This results in the influence of noise to the measurements being reduced and the accuracy of measuring blood oxygen under the condition of low perfusion being improved. In the process of the integral calculation, different confidences are set for different confidence intervals, which improves the accuracy of measuring blood oxygen under the condition of low perfusion.

Figure 5:
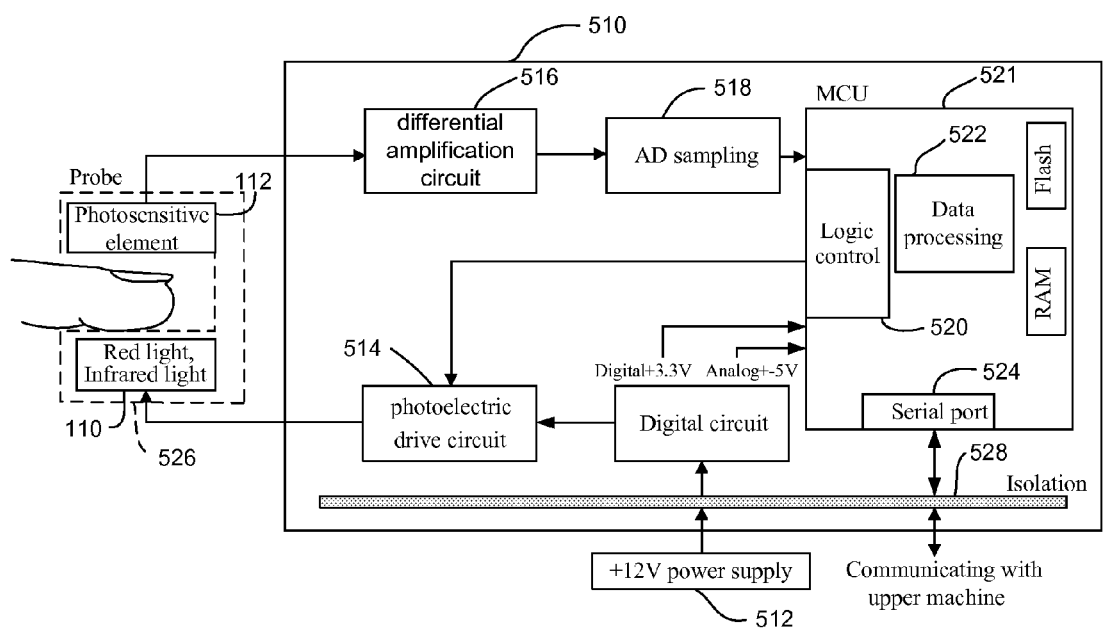
FIG. 5 is a schematic diagram of a circuit for measuring blood oxygen saturation according to an embodiment.

Referring now to FIG. 5, a process of measuring the blood oxygen saturation according to one embodiment is described. A circuit 510 for measuring the blood oxygen saturation is functionally divided into a power supply circuit 512, a photoelectric drive circuit 514, a signal amplification processing portion 516, an analog-to-digital (A/D) conversion circuit 518, a logic control portion 520, a single chip processor 521 with a data processing portion 522, and a serial port communication portion 524.

The power supply circuit 512, which is inputted ±12 V of AC/DC power supply, outputs two groups of power supplies: digital ±5V and analog ±5V, and provides the entire blood oxygen circuit board with power supplies in one embodiment.

The photoelectric drive circuit 514, which is adjusted by the logic control portion 520, outputs currents with different amplitudes to drive a light-emitting diode (LED) 110, such that the LED 110 can output signals of certain amplitude.

After converting the detected light signals into electrical signals (e.g., by a photosensitive element 112), a probe 526 sends the converted electrical signals to the amplification processing portion 516. After being subjected to differential amplification, background photo current cutoff processing, gain tuning, and bias current cutoff processing, the electrical signals are finally sent to the A/D converter 518 for conversion.

After converting the amplified analog signals into digital signals, the A/D conversion portion 518 sends the converted digital signals to the single chip processor 521 for processing.

The data converted by the A/D converter 518 is processed and calculated by the single chip processor data processing portion 522 to obtain pulse waves and the blood oxygen saturation.

The pulse waves and the blood oxygen saturation are sent outside via the serial port 524, and are insulated by optocouplers 528.

Further, the control of the single chip processor 521 on the circuits and portions are achieved through the logic control portion 520, such as a probe radiation time sequence control, a driving current control, a bias current control, a background photocurrent cutoff control, a signal A/D conversion control, and the like.

The blood oxygen saturation is calculated by adopting an area integral method, which is described as follows. The natural logarithm operation is performed on the red light signal $i_R$ and the infrared light signal $i_I$ to obtain signals $I_I$ and $I_R$, respectively. An interval [a, b] for $I_I(x)$ and $I_R(x)$ is defined, wherein the size of the interval [a, b] may be determined according to the actual requirement. The interval [a, b] is then divided into several equal subintervals, wherein dividing points are $a=x_0<x_1<x_2<\ldots<x_i<x_{i+1}<\ldots<x_n=b$. $\lambda$ is assumed as the length of $\Delta x_i=x_{i+1}-x_i$ (i=0, 1, 2, ..., n−1) and is in inverse proportion to the number of the dividing points. Taking any one point $x=\xi_i$ in each subinterval $[x_i, x_{i-1}]$, $x_i<\xi_i<x_{i+1}$ (i=0, 1, 2, ..., n−1), there is the following based on the formula of calculating blood oxygen by the differential method:

$$\frac{I_I(a) - I_I(x_1)}{I_R(a) - I_R(x_1)} = \frac{I_I(a) - I_I(x_2)}{I_R(a) - I_R(x_2)} \quad (6)$$
$$= \ldots$$
$$= \frac{I_I(a) - I_I(x_{i+1})}{I_R(a) - I_R(x_{i+1})}$$
$$= \ldots$$
$$= \frac{I_I(x_{n-1}) - I_I(b)}{I_R(x_{n-1}) - I_R(b)}$$
$$= R$$

$$\frac{\Delta \cdot (I_I(a) - I_1(x_1))}{\Delta \cdot (I_R(a) - I_R(x_1))} = \frac{2 \cdot \Delta \cdot (I_I(x_1) - I_1(x_2))}{2 \cdot \Delta \cdot (I_R(x_1) - I_R(x_2))}$$
$$= \ldots$$
$$= \frac{(i+1) \cdot \Delta \cdot (I_I(x_i) - I_1(x_{i+1}))}{(i+1) \cdot \Delta \cdot (I_R(x_i) - I_R(x_{i+1}))}$$
$$= \ldots$$
$$= \frac{n \cdot \Delta \cdot (I_I(x_{n-1}) - I_1(b))}{n \cdot \Delta \cdot (I_R(x_{n-1}) - I_R(b))}$$
$$= R$$

If numerators and denominator are accumulated respectively, there is:

$$\frac{[I_I(a) - I_I(x_1) + 2 \cdot (I_I(x_1) - I_I(x_2)) + \ldots +}{[I_R(a) - I_R(x_1) + 2 \cdot (I_R(x_1) - I_I(x_2)) + \ldots +} \quad (7)$$
$$\frac{(i+1) \cdot (I_I(x_i) - I_I(x_{i+1})) + \ldots + n \cdot (I_I(x_{n-1}) - I_I(b))] \cdot \Delta x}{(i+1) \cdot (I_R(x_i) - I_R(x_{i+1})) + \ldots + n \cdot (I_R(x_{n-1}) - I_R(b))] \cdot \Delta x} =$$

$$\frac{[I_I(a) + I_I(x_1) + \ldots + I_I(x_i) + \ldots +}{[I_R(a) + I_R(x_1) + \ldots + I_R(x_i) + \ldots +} \frac{I_I(x_{n-1}) - n \cdot I_I(b)] \cdot \Delta x}{I_R(x_{n-1}) - n \cdot I_R(b)] \cdot \Delta x} = \frac{\sum_{i=0}^{n-1}[I_I(x_i) - I_I(b)] \cdot \Delta x}{\sum_{i=0}^{n-1}[I_R(x_i) - I_R(b)] \cdot \Delta x} = R$$

If $n \to \infty, \lambda \to 0$ $$R = \frac{\lim_{\lambda \to 0}\sum_{i=0}^{n-1}[I_I(x_i) - I_I(b)] \cdot \Delta x}{\lim_{\lambda \to 0}\sum_{i=0}^{n-1}[I_R(x_i) - I_R(b)] \cdot \Delta x} = \frac{\int_a^b [I_I(x) - I_I(b)] \cdot dx}{\int_a^b [I_R(x) - I_R(b)] \cdot dx}.$$

It is explained from the above formula that the ratio of area A to area B in FIG. 2 corresponds to the value of blood oxygen. Thus, the signal of the pulse wave may perform the area integral instead of the conventional method of extremum ratio, which thus may eliminate the influence from white noise and nonwhite noise in the pulse wave to improve the accuracy of measuring blood oxygen under the condition of low perfusion.

Figure 6:
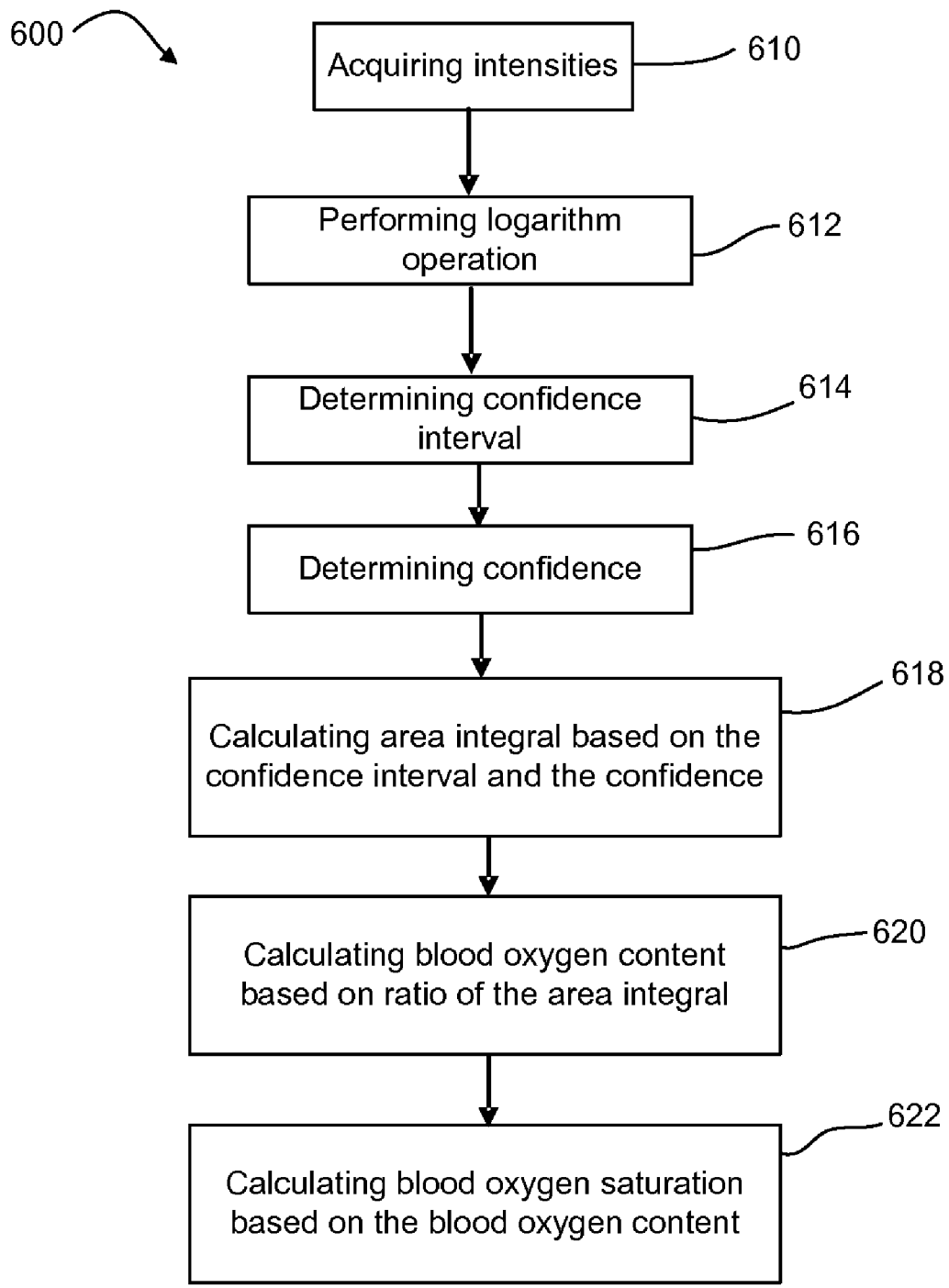
FIG. 6 is a flow diagram of a method for determining blood oxygen saturation according to an embodiment.

A method 600 suitable for measuring blood oxygen saturation under the condition of low perfusion according to one embodiment is shown in FIG. 6 and includes acquiring 610 intensities of the transmitted lights by transmitting a light of a first wavelength and a light of a second wavelength through organism tissues respectively, and converting the acquired intensities of the transmitted lights into signals corresponding to the light of the first wavelength and the light of the second wavelength. The light of the first wavelength and the light of the second wavelength are generally the red light with a wavelength of approximately 660 nm and the infrared light with a wavelength of approximately 940 nm respectively. After the two lights are irradiated to the organism tissues (e.g., human tissue peripherals), and current signals $i_R$ and $i_I$ corresponding to the transmitted lights obtained by irradiating the red light and the infrared light respectively are detected and converted into digital signals via A/D conversion.

The method 600 also includes performing 612 logarithmic operations on the two signals $i_I$ and $i_R$ to obtain signals $I_I$ and $I_R$, respectively.

The method 600 also includes determining 614 a confidence interval. It may be seen from FIG. 4 that while an interference signal is superposed on the waveform and there are greater changes in the wave peaks, it is relatively clear in the wave valleys. This is because there is a short process time (generally between approximately 70 and approximately 120 ms) for human cardiac ejection and a relatively faster velocity of blood flow. Thus, as shown in FIG. 4, the interval ab is less influenced by noise for the process wherein blood in the vessel goes from minimum to maximum, while in the interval bc prior to cardiac ejecting, interference increases due to the longer process time and a relatively slow velocity of blood flow.

The calculation of blood oxygen saturation is divided into different confidential intervals according to different degrees of noise interference within the pulse fluctuation period, i.e., the intervals interfered with greatly have low confidence, and the intervals interfered with least have high confidence.

The determination 614 of the confidence intervals according to one embodiment is as follows. First, the signal over a period of time is extracted, and then the wave valleys in each pulse cycle of the signal for the red light and those of the signal for the infrared light are searched respectively from the signal over the period of time, to obtain the positions $V_{R1}$, $V_{R2}, V_{Rj} \ldots V_{Rn}$ of the wave valleys of the signal for the red light and the positions $V_{I1}, V_{I2}, V_{Ij} \ldots V_{In}$ of the wave valleys of the signal of the infrared light, where j is the jth pulse cycle.

The positions $M_{R1}, M_{R2}, M_{Rj} \ldots M_{Rn}$ of the wave peaks of the signal for the red light and the positions $M_{I1}, M_{I2}, M_{Ij} \ldots M_{In}$ of the wave peaks of the signal for the infrared light are determined based on the position of each wave valley. Thus the wave peaks and the wave valleys of each of the red light and the infrared light in each pulse cycle are obtained.

Figure 7:
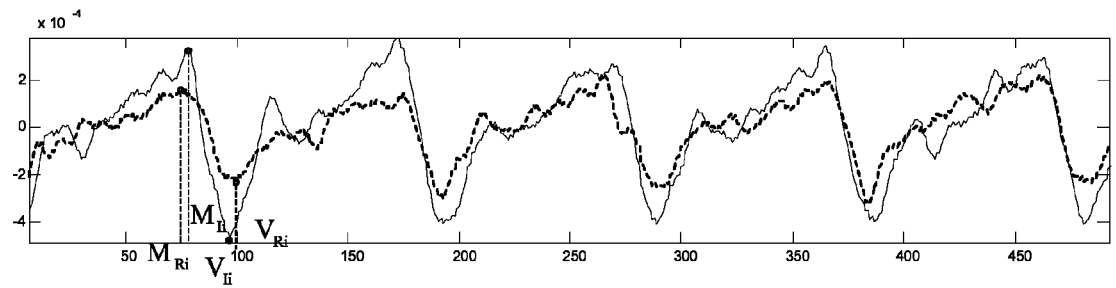
FIG. 7 is a schematic diagram of the position of the peaks and valleys of a wave of red light and a wave of infrared light.

The method for determining 614 the confidence interval continues by determining the length L of the fall edge of each pulse cycle as follows. Since there are interferences, in many cases, the wave peaks and the wave valleys of the red light do not correspond to the wave peaks and the wave valleys of the infrared light (that is, for the positions of the peaks and valleys of the two signals, the two wave peaks and the two wave valleys are not present at the same time due to the influence of noise and interference, which is referred to as noncorrespondence). After the noncorrespondence of the peaks and the valleys is cancelled, the positions of the wave valleys and the wave peaks for the i-th waveform are respectively $M_{Ri}, M_{Ii}$, $V_{Ri}, V_{Ii}$, as illustrated in FIG. 7.

When min $(V_{Ri}, V_{Ii})<=$max $(M_{Ri}, M_{Ii})$, this time calculation of blood oxygen is cancelled because max $(M_{Ri}, M_{Ii})$ represents the positions of the wave peaks presented later and min $(V_{Ri}, V_{Ii})$ represents the positions of the wave valleys presented earlier. If the wave valleys of signal "a" occur earlier than the wave peaks of signal "b," this shows that there is so much interference in the signals or error in searching the peaks and the valleys that the value of blood oxygen cannot be calculated. If performing the calculation, the result would be wrong.

When min $(V_{Ri}, V_{Ii})>$max $(M_{Ri}, M_{Ii})$, the length L of the fall edge is determined as L=min $(V_{Ri}, V_{Ii})-$max $(M_{Ri}, M_{Ii})$, where $V_{Ri}$ and $M_{Ri}$ are respectively the positions of the wave peak and the wave valley in the i-th pulse cycle of the signal for the red light, $V_{Ii}$ and $M_{Ii}$ are respectively the positions of the wave peak and the wave valley in the i-th pulse cycle of the signal for the infrared light, and i is any value between 1 and n.

The method for determining 614 the confidence interval continues by determining the interval of the rise edge in the i-th pulse cycle as $[V_{ri}, M_{ri}]$, and the interval of the fall edge in the i-th pulse cycle as $[M_{fi}, V_{fi}]$, where $$V_{ri} = \max(V_{R(i-1)}, V_{I(i-1)}),$$

$$M_{ri} = \min(M_{Ri}, M_{Ii}),$$

$$M_{fi} = \max(M_{Ri}, M_{Ii}) + L \times 0.1,$$

$$V_{fi} = \min(V_{Ri}, V_{Ii}) - L \times 0.1.$$

When the interval $[M_{fi}, V_{fi}]$ of the fall edge is calculated, one-tenth at right and one-tenth at left of the intervals of the wave peaks and the wave valleys are cut off, that is, only the 80 percent of the length of the interval is calculated, which may reduce calculation error caused by the noncorrespondence of the peaks and the valleys.

As the signal waveform is from a discrete signal sampled by a fixed sampling rate, the discrete form of the integral is used in the calculation of blood oxygen in formula (7):

The blood oxygen content of the interval of the fall edge is:

$$R_{fi} = \frac{\int_{M_{fi}}^{V_{fi}} [I_i(x) - I_i(V_{fi})] dx}{\int_{M_{fi}}^{V_{fi}} [R_i(x) - R_i(V_{fi})] dx} = \frac{\sum_{i-1}^{n-1} [I_i(x) - I_i(V_{fi})]}{\sum_{i-1}^{n-1} [R_i(x) - R_i(V_{fi})]}$$

The blood oxygen content of the interval of the rise edge is:

$$R_{ri} = \frac{\int_{M_{ri}}^{V_{ri}} [I_i(x) - I_i(V_{ri})] dx}{\int_{M_{ri}}^{V_{ri}} [R_i(x) - R_i(V_{ri})] dx} = \frac{\sum_{i-1}^{n-1} [I_i(x) - I_i(V_{ri})]}{\sum_{i-1}^{n-1} [R_i(x) - R_i(V_{ri})]}$$

Returning to FIG. 6, the method 600 also includes determining 616 confidence. The confidence of the rise edge and the fall edge are defined as $\sigma_r$ and $\sigma_f$, respectively, and $\sigma_f$ is higher than $\sigma_r$. The values of $\sigma_f$ and $\sigma_r$ are respectively taken as according to experience:

$$\sigma_r = 0.25 \times (0.8 - \gamma_{v-1} \gamma_m),$$

$$\sigma_f = 0.8 \gamma_v - \gamma_m,$$

where $\gamma_m$ is the fluctuation coefficient of the wave peaks in the i-th pulse cycle, and $\gamma_v$ is the fluctuation coefficient of the wave valleys in the i-th pulse cycle, $$\gamma_m = \frac{|M_{Ri} - M_{Ii}|}{L}$$

$$\gamma_v = \frac{|V_{Ri} - V_{Ii}|}{L}.$$

The fluctuation coefficients of the wave peaks and the wave valleys provide evidence for the confidence of blood oxygen. When $\gamma_m$ or $\gamma_v$ is more than 0.4, the confidence of the blood oxygen is 0, that is, the calculation of the blood oxygen at this cycle is cancelled. According to the above formula, the larger $\gamma_v$ (or $\gamma_m$) is, the larger the noncorrespondence is between the position of the wave peak (or the wave valley) of the red light and the position of the wave peak (or the wave valley) of the infrared light. When $\gamma_m$ or $\gamma_v$ is more than 0.4, there is so much interference in the signals or error in searching the peaks and the valleys that the value of blood oxygen cannot be calculated.

The method 600 also includes calculating 618 integral areas in the i-th pulse cycle of the two lights according to the confidence interval and the confidence. The value of R in the i-th pulse cycle is:

$$R_i = \frac{\sigma_r \cdot R_{ri} + \sigma_f \cdot R_{fi}}{\sigma_r + \sigma_f}.$$

That is, the blood oxygen value is the sum of the weighted blood oxygen contents of subsections with the confidence as a weight coefficient. The blood oxygen content within the signal of this section is derived from the sum of the weighted blood oxygen contents of 1 to n pulse cycles.

The method 600 also includes calculating 620 blood oxygen content based on the ratio of the area integral and calculating 622 blood oxygen saturation based on the blood oxygen content:

$$SpO_2 = (A \times R + B)/(C \times R + D),$$

where $SpO_2$ is the blood oxygen saturation;

A=$\epsilon_4$;
B=$-\epsilon_2$;
C=$\epsilon_4 - \epsilon_3$;
D=$\epsilon_1 - \epsilon_2$;

$\epsilon_1$, $\epsilon_2$ are respectively the absorption rate of oxyhemoglobin ($HbO_2$) to the red light and that of deoxyhemoglobin (Hb) to the red light; and $\epsilon_3$, $\epsilon_4$ are respectively the absorption rate of oxyhemoglobin to the infrared light and that of deoxyhemoglobin to the infrared light.

Figure 8:
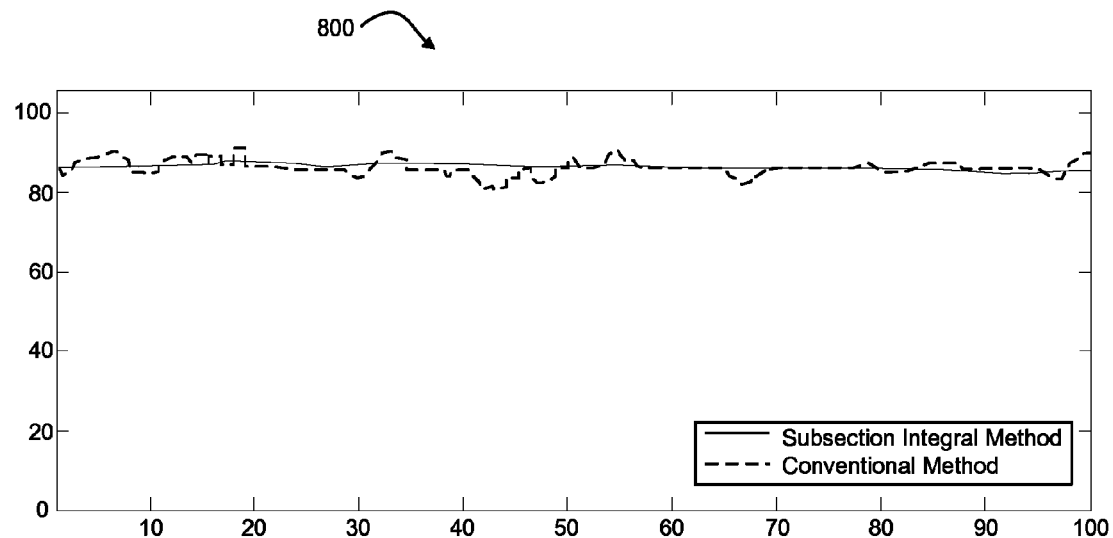
FIG. 8 is a trend chart of the blood oxygen calculated in an embodiment disclosed herein and a conventional algorithm.

FIG. 8 is a trend contrast chart 800 of the blood oxygen contents calculated by the subsection integral method according to one embodiment and the conventional method. It can be seen from the figure that it is more stable and accurate for the result calculated by the embodiments disclosed herein.

Figure 9:
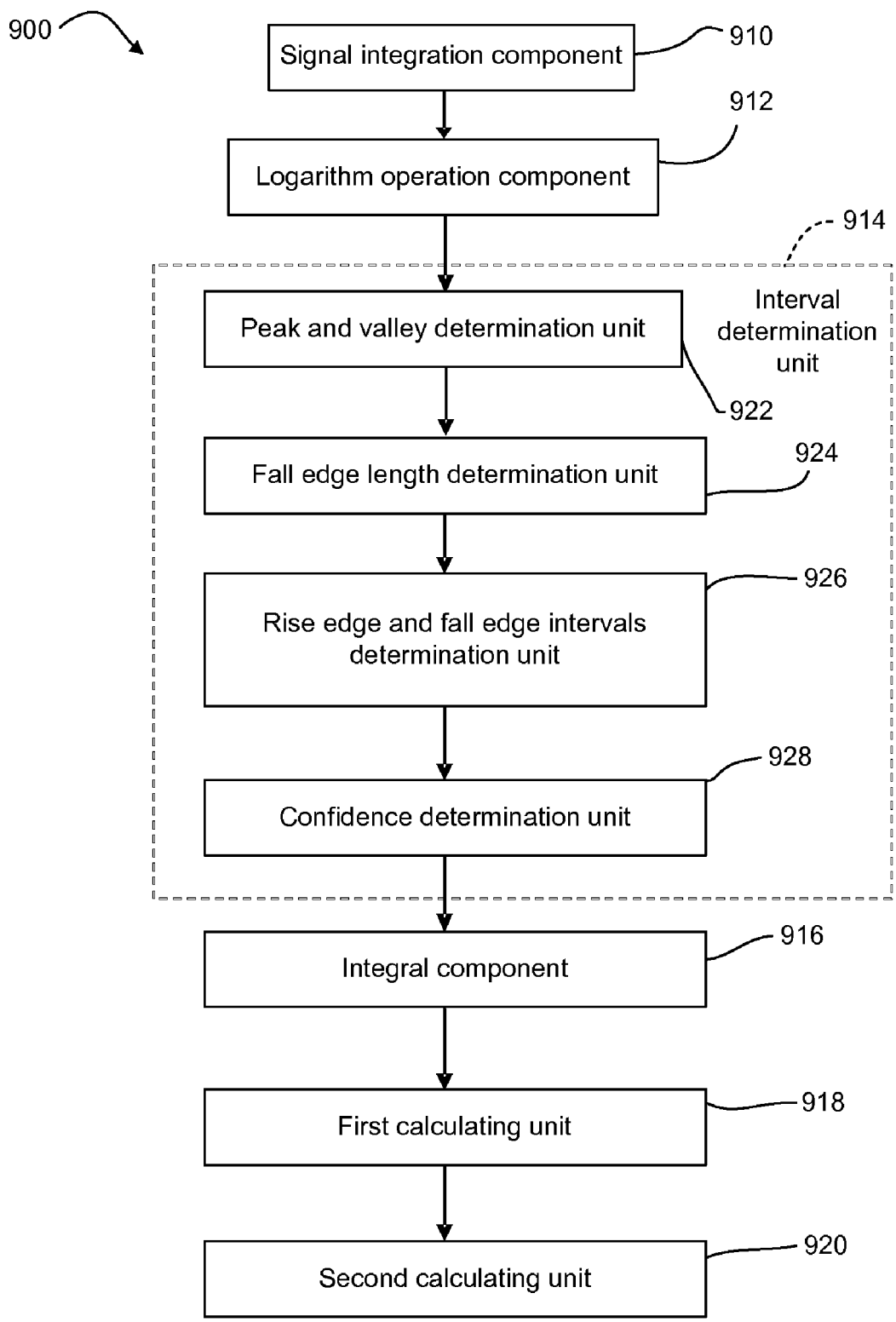
FIG. 9 is a schematic diagram of a system for measuring blood oxygen saturation according to an embodiment.

An apparatus 900 according to the above mentioned method is shown in FIG. 9, which comprises a signal generation component 910, a logarithm operation component 912, an interval determination component 914, an integral component 916, a first calculating component 918, and a second calculating component 920. The signal generation component 910 is used to acquire intensities of the transmitted lights that are obtained by transmitting a light of a first wavelength and a light of a second wavelength through organism tissues and to convert the acquired intensities of the transmitted lights into corresponding signals for the light of the first wavelength and the light of the second wavelength. The logarithm operation component 912 is used to perform a natural logarithm operation on the signals for the light of the first wavelength and the light of the second wavelength respectively and output the result to the integral component 916.

The interval determination component 914 is used to define at least one interval on the waveforms of the signals for the light of the first wavelength and the light of the second wavelength. The integral component 916 is used to perform an area integral on the signals for the light of the first wavelength and the light of the second wavelength within the at least one interval. The first calculating component 918 is used to calculate the ratio of the total area integral of the signal for the light of the first wavelength to the total area integral of the signal for the light of the second wavelength as the blood oxygen content R. The second calculating component 920 is used to calculate the blood oxygen saturation based on the formula $SpO_2=(A \times R+B)/(C \times R+D)$.

In one embodiment, the interval determination component 914 is used to divide the at least one interval into different confidence intervals according to the different degrees of the noise interference within the pulse fluctuation cycle, and the confidence for the interval with greater interference is less than the confidence for the interval with lower interference. The integral component 916 is further used to calculate the total area integral of the signal for the light of the first wavelength and the total area integral of the signal for the light of the second wavelength according to the confidence of each confidence interval.

The confidence intervals include a rise edge interval in which the signal for the light of the first wavelength and the signal for the light of the second wavelength are at rise stage and a fall edge interval in which the signal for the light of the first wavelength and the signal for the light of the second wavelength are at fall stage, wherein the confidence of the rise edge interval is less than the confidence of the fall edge interval.

In one embodiment, the interval determination component 914 includes a peak and valley determination unit 922, a fall edge length determination unit 924, a rise edge and fall edge intervals determination unit 926, and a confidence determination unit 928.

The peak and valley determination unit 922 is used to respectively search the wave valley in each pulse cycle of the signal for the light of the first wavelength and the wave valley in each pulse cycle of the signal for the light of the second wavelength from the signal over a period of time to obtain positions $V_{R1}, V_{R2}, V_{Rj} \ldots V_{Rn}$ of the wave valleys of the signal for the light of the first wavelength and positions $V_{I1}, V_{I2}, V_{Ij} \ldots V_{In}$ of the wave valleys of the signal for the light of the second wavelength, where j is the j-th pulse cycle, and to determine positions $M_{R1}, M_{R2}, M_{Rj} \ldots M_{Rn}$ of the wave peaks of the signal for the light of the first wavelength and positions $M_{I1}, M_{I2}, M_{Ij} \ldots M_{In}$ of the wave peaks of the signal for the light of the second wavelength based on the positions of the wave valleys.

The fall edge length determination unit 924 is used to determine, based on the values of the wave peak and the wave valley of each pulse cycle, a length L of the fall edge of the pulse cycle, $L=\min(V_{Ri}, V_{Ii})-\max(M_{Ri}, M_{Ii})$, where $V_{Ri}$, $M_{Ri}$ are respectively positions of the wave peak and the wave valley in the i-th pulse cycle of the signal for the light of the first wavelength, $V_{Ii}$, $M_{Ii}$ are respectively positions of the wave peak and the wave valley in the i-th pulse cycle of the signal for the light of the second wavelength, and i is any value between 1 and n.

The rise edge and fall edge intervals determination unit 926 is used to determine the rise interval and the fall interval in the i-th pulse cycle based on the values of the wave peak and the wave valley and the length L of the fall edge in the i-th pulse cycle. The rise edge interval is $[V_{ri}, M_{ri}]$ and the fall edge interval is $[M_{fi}, V_{fi}]$, wherein $V_{ri}=\max(V_{R(i-1)}, V_{I(i-1)})$, $M_{ri}=\min(M_{Ri}, M_{Ii})$, $M_{fi}=\max(M_{Ri}, M_{Ii})+L \times 0.1$, and $V_{fi}=\min(V_{Ri}, V_{Ii})-L \times 0.1$.

The confidence determination unit 928 is used to determine the confidences of the rise edge interval and the fall edge interval, wherein the confidence of the rise edge interval is $\sigma_r$, the confidence of the fall edge interval is $\sigma_f$, and $$\sigma_r=0.25 \times (0.8-\gamma_{v-1}-\gamma_m),$$

$$\sigma_f=0.8-\gamma_v-\gamma_m,$$

where $\gamma_m$ is the fluctuation coefficient of the wave peak in the i-th pulse cycle and $\gamma_v$ is the fluctuation coefficient of the wave valley at the i-th pulse cycle.

After a system powers on, according to one embodiment, the hardware is initialized, the CPU system performs a self check, and the program is initialized. Once the above processes are finished, the system accesses a core control module. A measurement apparatus collects data in real time and the measured data is stored in a data buffer. The core algorithm processes the data to calculate blood oxygen and pulse rate parameters as described herein. The control apparatus performs different controls on the hardware in all states based on the measured value, and controls A/D (including internal A/D and external A/D) sampling, and controls drive current of the luminous tube (e.g., LED) and the bias circuit and gains. The core algorithm is used to calculate the value of subsection integral and the pulse rate is calculated. Then, as discussed above, the blood oxygen is calculated by using different confidences.

The light of the first wavelength and the light of the second wavelength in the above embodiments may also be the lights of other different wavelengths.

The above disclosure describes the invention in detail in conjunction with specific example embodiments, but the invention should not be considered to be limited to the example embodiments. Those skilled in the art should understand that various modifications and changes may be made without departing from the essence of the invention and should be considered to fall into the scope of the invention.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

It will be obvious to those having skill in the art that many changes may be made to the details of the above-described embodiments without departing from the underlying principles of the invention. The scope of the present invention should, therefore, be determined only by the following claims.

What is claimed is:

1. A method for measuring blood oxygen saturation, the method comprising:

acquiring intensities of transmitted lights that are obtained by transmitting respectively a light of a first wavelength and a light of a second wavelength through organism tissues, and converting the intensities of the transmitted lights into corresponding signals for the light of the first wavelength and the light of the second wavelength;

defining at least one interval on waveforms of the signals for the light of the first wavelength and the light of the second wavelength, and performing an area integral on the waveforms of the signals for the light of the first wavelength and the light of the second wavelength in the at least one interval to produce a total area integral of the signal for the light of the first wavelength and a total area integral of the signal for the light of the second wavelength;

calculating a ratio of the total area integral of the signal for the light of the first wavelength to the total area integral of the signal for the light of the second wavelength as a blood oxygen content R; and calculating a blood oxygen saturation according to the following formula:

$$SpO_2 = (A \times R + B)/(C \times R + D),$$

where $SpO_2$ is the blood oxygen saturation;
$A = \epsilon_4$;
$B = -\epsilon_2$;
$C = \epsilon_4 - \epsilon_3$;
$D = \epsilon_1 - \epsilon_2$;
$\epsilon_1$, $\epsilon_2$ are respectively an absorption rate of oxyhemoglobin to the light of the first wavelength and an absorption rate of deoxyhemoglobin to the light of the first wavelength; and
$\epsilon_3$, $\epsilon_4$ are respectively an absorption rate of oxyhemoglobin to the light of the second wavelength and an absorption rate of deoxyhemoglobin to the light of the second wavelength;

wherein the at least one interval is divided into different confidence intervals according to different degrees of noise interference in a pulse fluctuation cycle, wherein a confidence value of one confidence interval with relatively high interference is less than that of another confidence interval with relatively low interference, wherein the total area integral of the signal for the light of the first wavelength comprises a sum of products of the area integral of the waveform of the signal for the light of the first wavelength in all the confidence intervals and the corresponding confidence, and wherein the total area integral of the signal for the light of the second wavelength comprises a sum of products of the area integral of the waveform of the signal for the light of the second wavelength in all the confidence intervals and the corresponding confidence.

2. The method of claim 1, further comprising:
before defining the at least one interval, performing respectively a natural logarithm operation on the signal for the light of the first wavelength and the signal for the light of the second wavelength.

3. The method of claim 1, wherein the confidence intervals include a rise stage interval in which the signal for the light of the first wavelength and the signal for the light of the second wavelength are at a rise edge, and a fall edge interval in which the signal for the light of the first wavelength and the signal for the light of the second wavelength are at a fall edge, wherein the confidence of the rise edge interval is less than the confidence of the fall edge interval.

4. The method of claim 3, wherein determining the rise edge interval and the fall edge interval comprises:

searching a wave valley in each pulse cycle of the signal for the light of the first wavelength and a wave valley in each pulse cycle of the signal for the light of the second wavelength from the signal over a period of time to obtain positions $V_{R1}, V_{R2}, V_{Rj} \ldots V_{Rn}$ of the wave valleys of the signal for the light of the first wavelength and positions $V_{I1}, V_{I2}, V_{Ij} \ldots V_{In}$ of the wave valleys of the signal for the light of the second wavelength, where j is the jth pulse cycle;

determining positions $M_{R1}, M_{R2}, M_{Rj} \ldots M_{Rn}$ of wave peaks of the signal for the light of the first wavelength and positions $M_{I1}, M_{I2}, M_{Ij} \ldots M_{In}$ of wave peaks of the signal for the light of the second wavelength based on the positions of the wave valleys;

determining, based on the values of the wave peak and the wave valley of each pulse cycle, a length L of the fall edge of the pulse cycle, $$L = \min(V_{Ri}, V_{Ii}) - \max(M_{Ri}, M_{Ii}),$$

where $V_{Ri}$, $M_{Ri}$ are respectively positions of the wave peak and the wave valley in the i-th pulse cycle of the signal for the light of the first wavelength, $V_{Ii}$, $M_{Ii}$ are respectively positions of the wave peak and the wave valley in the i-th pulse cycle of the signal for the light of the second wavelength, and i is any value between 1 and n; and determining the rise interval $[V_{ri}, M_{ri}]$ and the fall interval $[M_{fi}, V_{fi}]$ in the i-th pulse cycle based on the values of the wave peak and the wave valley and the length L of the fall edge in the i-th pulse cycle, wherein $V_{ri} = \max(V_{R(i-1)}, V_{I(i-1)})$, $M_{ri} = \min(M_{Ri}, M_{Ii})$, $M_{fi} = \max(M_{Ri}, M_{Ii}) + L \times 0.1$, and $V_{fi} = \min(V_{Ri}, V_{Ii}) - L \times 0.1$.

5. The method of claim 4, wherein in determining the length L of the fall edge, when $\min(V_{Ri}, V_{Ii}) <= \max(M_{Ri}, M_{Ii})$, the corresponding time calculation of the blood oxygen is cancelled, and when $\min(V_{Ri}, V_{Ii}) >= \max(M_{Ri}, M_{Ii})$, the length L of the fall edge is determined as:

$$L = \min(V_{Ri}, V_{Ii}) - \max(M_{Ri}, M_{Ii}).$$

6. The method of claim 4, wherein the confidence of the rise interval edge is $\sigma_r$, and the confidence of the fall edge interval is $\sigma_f$, wherein $$\sigma_r = 0.25 \times (0.8 - \gamma_{v-1} - \gamma_m),$$

$$\sigma_f = 0.8 - \gamma_v - \gamma_m,$$

where $\gamma_m$ is a fluctuation coefficient of the wave peak in the i-th pulse cycle and $\gamma_v$ is a fluctuation coefficient of the wave valley in the i-th pulse cycle, $$\gamma_m = \frac{|M_{Ri} - M_{Ii}|}{L}$$

$$\gamma_v = \frac{|V_{Ri} - V_{Ii}|}{L}.$$

7. The method of claim 6, wherein the blood oxygen content of the i-th pulse cycle is:

$$R_i = \frac{\sigma_r \cdot R_{ri} + \sigma_f \cdot R_{fi}}{\sigma_r + \sigma_f}.$$

8. The method of claim 7, wherein when the fluctuation coefficient of the wave peak or the wave valley is more than 0.4, the confidence of the blood oxygen content in the corresponding pulse cycle is zero.

9. An apparatus for measuring blood oxygen saturation, the apparatus comprising:
a signal generation component to acquire intensities of transmitted lights that are obtained by transmitting a light of a first wavelength and a light of a second wavelength through organism tissues and to convert the acquired intensities of the transmitted lights into corresponding signals for the light of the first wavelength and the light of the second wavelength;
an interval determination component to define at least one interval on waveforms of the signals for the light of the first wavelength and the light of the second wavelength;
an integral component to perform a natural logarithm operation on the signals for the light of the first wavelength and the light of the second wavelength in the at least one interval respectively;
a first calculating component to calculate a ratio of the total area integral of the signal for the light of the first wavelength to the total area integral of the signal for the light of the second wavelength as the blood oxygen content R; and
a second calculating component to calculate blood oxygen saturation according to the following formula:

$SpO_2=(A \times R+B)/(C \times R+D)$, where $SpO_2$ is the blood oxygen saturation;
$A=\epsilon_4$;
$B=-\epsilon_2$;
$C=\epsilon_4-\epsilon_3$;
$D=\epsilon_1-\epsilon_2$;
$\epsilon_1$, $\epsilon_2$ are respectively an absorption rate of oxyhemoglobin to the red light and an absorption rate of deoxyhemoglobin to the red light; and
$\epsilon_3$, $\epsilon_4$ are respectively an absorption rate of oxyhemoglobin to the infrared light and an absorption rate of deoxyhemoglobin to the infrared light;
wherein the interval determination component is used to divide the at least one interval into different confidence intervals according to the different degrees of the noise interference within the pulse fluctuation cycle, and the confidence for the interval with greater interference is less than the confidence for the interval with lower interference, and the integral component is further used to calculate the total area integral of the signal for the light of the first wavelength and the total area integral of the signal for the light of the second wavelength according to the confidence of each confidence interval.

10. The apparatus of claim 9, further comprising:
a logarithm operation component to perform a natural logarithm operation on the signals for the light of the first wavelength and the light of the second wavelength respectively and to output the result to the integral component.

11. The apparatus of claim 9, wherein the confidence intervals include a rise edge interval in which the signal for the light of the first wavelength and the signal for the light of the second wavelength are at rise stage and a fall edge interval in which the signal for the light of the first wavelength and the signal for the light of the second wavelength are at fall stage, wherein the confidence of the rise edge interval is less than the confidence of the fall edge interval.

12. The apparatus of claim 11, wherein the interval determination component includes:
a peak and valley determination unit to respectively search a wave valley in each pulse cycle of the signal for the light of the first wavelength and a wave valley in each pulse cycle of the signal for the light of the second wavelength from the signal over a period of time to obtain positions $V_{R1}, V_{R2}, V_{Rj} \ldots V_{Rn}$ of the wave valleys of the signal for the light of the first wavelength and positions $V_{I1}, V_{I2}, V_{Ij} \ldots V_{In}$ of the wave valleys of the signal for the light of the second wavelength, where j is the jth pulse cycle, and to determine positions $M_{R1}, M_{R2}, M_{Rj} \ldots M_{Rn}$ of wave peaks of the signal for the light of the first wavelength and positions $M_{I1}, M_{I2}, M_{Ij} \ldots M_{In}$ of wave peaks of the signal for the light of the second wavelength based on the positions of the wave valleys;
a fall edge length determination unit to determine, based on the values of the wave peak and the wave valley of each pulse cycle, a length L of the fall edge of the pulse cycle, $L=\min(V_{Ri},V_{Ii})-\max(M_{Ri},M_{Ii})$, where $V_{Ri}$, $M_{Ri}$ are respectively positions of the wave peak and the wave valley in the i-th pulse cycle of the signal for the light of the first wavelength, $V_{Ii}$, $M_{Ii}$, are respectively positions of the wave peak and the wave valley in the i-th pulse cycle of the signal for the light of the second wavelength, and i is any value between 1 and n; and
a rise edge and fall edge intervals determination unit to determine the rise interval and the fall interval in the i-th pulse cycle based on the values of the wave peak and the wave valley and the length L of the fall edge in the i-th pulse cycle, wherein the rise edge interval is $[V_{ri}, M_{ri}]$ and the fall edge interval is $[M_{fi}, V_{fi}]$, wherein $V_{ri}=\max (V_{R(i-1)}, V_{I(i-1)})$, $M_{ri}=\min (M_{Ri}, M_{Ii})$, $M_{fi}=\max (M_{Ri}, M_{Ii})+L \times 0.1$, and $V_{fi}=\min (V_{Ri}, V_{Ii})-L \times 0.1$.

13. The apparatus of claim 12, wherein the interval determination component further includes a confidence determination unit to determine confidences of the rise edge interval and the fall edge interval, wherein the confidence of the rise edge interval is $\sigma_r$, the confidence of the fall edge interval is $\sigma_f$, and $\sigma_r=0.25 \times (0.8-\gamma_{v-1}-\gamma_m)$, $\sigma_f=0.8-\gamma_v-\gamma_m$, where $\gamma_m$ is a fluctuation coefficient of the wave peak in the i-th pulse cycle and $\gamma_v$ is a fluctuation coefficient of the wave valley at the i-th pulse cycle, $$\gamma_m = \frac{|M_{Ri} - M_{Ii}|}{L}$$

$$\gamma_v = \frac{|V_{Ri} - V_{Ii}|}{L}.$$

14. The apparatus of claim 13, wherein the blood oxygen content in the i-th pulse cycle is:

$$R_i = \frac{\sigma_r \cdot R_{ri} + \sigma_f \cdot R_{fi}}{\sigma_r + \sigma_f}.$$

15. A non-transitory, computer-readable medium comprising program code for performing a method for measuring blood oxygen saturation, the method comprising:
acquiring intensities of transmitted lights that are obtained by transmitting respectively a light of a first wavelength and a light of a second wavelength through organism tissues, and converting the intensities of the transmitted lights into corresponding signals for the light of the first wavelength and the light of the second wavelength;

defining at least one interval on waveforms of the signals for the light of the first wavelength and the light of the second wavelength, and performing an area integral on the waveforms of the signals for the light of the first wavelength and the light of the second wavelength in the at least one interval to produce a total area integral of the signal for the light of the first wavelength and a total area integral of the signal for the light of the second wavelength;

calculating a ratio of the total area integral of the signal for the light of the first wavelength to the total area integral of the signal for the light of the second wavelength as a blood oxygen content R; and calculating a blood oxygen saturation according to the following formula:

$$SpO_2 = (A \times R + B)/(C \times R + D),$$

where $SpO_2$ is the blood oxygen saturation;
$A = \epsilon_4$;
$B = -\epsilon_2$;
$C = \epsilon_4 - \epsilon_3$;
$D = \epsilon_1 - \epsilon_2$;
$\epsilon_1$, $\epsilon_2$ are respectively an absorption rate of oxyhemoglobin to the light of the first wavelength and an absorption rate of deoxyhemoglobin to the light of the first wavelength; and
$\epsilon_3$, $\epsilon_4$ are respectively an absorption rate of oxyhemoglobin to the light of the second wavelength and an absorption rate of deoxyhemoglobin to the light of the second wavelength;

wherein the at least one interval is divided into different confidence intervals according to different degrees of noise interference in a pulse fluctuation cycle, wherein a confidence value of one confidence interval with relatively high interference is less than that of another confidence interval with relatively low interference, wherein the total area integral of the signal for the light of the first wavelength comprises a sum of products of the area integral of the waveform of the signal for the light of the first wavelength in all the confidence intervals and the corresponding confidence, and wherein the total area integral of the signal for the light of the second wavelength comprises a sum of products of the area integral of the waveform of the signal for the light of the second wavelength in all the confidence intervals and the corresponding confidence.

16. The computer-readable medium of claim 15, wherein the confidence intervals include a rise stage interval in which the signal for the light of the first wavelength and the signal for the light of the second wavelength are at a rise edge, and a fall edge interval in which the signal for the light of the first wavelength and the signal for the light of the second wavelength are at a fall edge, wherein the confidence of the rise edge interval is less than the confidence of the fall edge interval.

17. The computer-readable medium of claim 16, wherein determining the rise edge interval and the fall edge interval comprises:

searching a wave valley in each pulse cycle of the signal for the light of the first wavelength and a wave valley in each pulse cycle of the signal for the light of the second wavelength from the signal over a period of time to obtain positions $V_{R1}, V_{R2}, V_{Rj} \ldots V_{Rn}$ of the wave valleys of the signal for the light of the first wavelength and positions $V_{I1}, V_{I2}, V_{Ij} \ldots V_{In}$ of the wave valleys of the signal for the light of the second wavelength, where j is the jth pulse cycle;

determining positions $M_{R1}, M_{R2}, M_{Rj} \ldots M_{Rn}$ of wave peaks of the signal for the light of the first wavelength and positions $M_{I1}, M_{I2}, M_{Ij} \ldots M_{In}$ of wave peaks of the signal for the light of the second wavelength based on the positions of the wave valleys;

determining, based on the values of the wave peak and the wave valley of each pulse cycle, a length L of the fall edge of the pulse cycle, $$L = \min(V_{Ri}, V_{Ii}) - \max(M_{Ri}, M_{Ij}),$$

where $V_{Ri}$, $M_{Ri}$ are respectively positions of the wave peak and the wave valley in the i-th pulse cycle of the signal for the light of the first wavelength, $V_{Ii}$, $M_{Ii}$, are respectively positions of the wave peak and the wave valley in the i-th pulse cycle of the signal for the light of the second wavelength, and i is any value between 1 and n; and determining the rise interval $[V_{ri}, M_{ri}]_i$ and the fall interval $[M_{fi}, V_{fi}]$ in the i-th pulse cycle based on the values of the wave peak and the wave valley and the length L of the fall edge in the i-th pulse cycle, wherein $V_{ri} = \max(V_{R(i-1)}, V_{I(i-1)})$, $M_{ri} = \min(M_{Ri}, M_{Ii})$, $M_{fi} = \max(M_{Ri}, M_{Ii}) + L \times 0.1$, and $V_{fi} = \min(V_{Ri}, V_{Ii}) - L \times 0.1$.

18. The computer-readable medium of claim 17, wherein in determining the length L of the fall edge, when $\min(V_{Ri}, V_{Ii}) \leq \max(M_{Ri}, M_{Ii})$, the corresponding time calculation of the blood oxygen is cancelled, and when $\min(V_{Ri}, V_{Ii}) > \max(M_{Ri}, M_{Ii})$, the length L of the fall edge is determined as:

$$L = \min(V_{Ri}, V_{Ii}) - \max(M_{Ri}, M_{Ii}).$$

19. The computer-readable medium of claim 17, wherein the confidence of the rise interval edge is $\sigma_r$, and the confidence of the fall edge interval is $\sigma_f$, wherein $$\sigma_r = 0.25 \times (0.8 - \gamma_{v-1} - \gamma_m),$$

$$\sigma_f = 0.8 - \gamma_v - \gamma_m,$$

where $\gamma_m$ is a fluctuation coefficient of the wave peak in the i-th pulse cycle and $\gamma_v$ is a fluctuation coefficient of the wave valley in the i-th pulse cycle, $$\gamma_m = \frac{|M_{Ri} - M_{Ii}|}{L}$$

$$\gamma_v = \frac{|V_{Ri} - V_{Ii}|}{L}.$$

20. The computer-readable medium of claim 19, wherein the blood oxygen content of the i-th pulse cycle is:

$$R_i = \frac{\sigma_r \cdot R_{ri} + \sigma_f \cdot R_{fi}}{\sigma_r + \sigma_f}.$$

21. The computer-readable medium of claim 20, wherein when the fluctuation coefficient of the wave peak or the wave valley is more than 0.4, the confidence of the blood oxygen content in the corresponding pulse cycle is zero.

22. A system for measuring blood oxygen saturation, the system comprising:

means for acquiring intensities of a first light at a first wavelength and a second light at a second wavelength transmitted through organism tissues and for converting the acquired intensities of the transmitted lights into signals corresponding to the light of the first wavelength and the light of the second wavelength;

means for defining at least one interval on waveforms of the signals for the light of the first wavelength and the light of the second wavelength;

means for performing a natural logarithm operation on the signals for the light of the first wavelength and the light of the second wavelength in the at least one interval;

means for calculating a ratio of the total area integral of the signal for the light of the first wavelength to the total area integral of the signal for the light of the second wavelength as the blood oxygen content R; and means for calculating blood oxygen saturation according to the following formula:

$SpO_2=(A\times R+B)/(C\times R+D)$, where $SpO_2$ is the blood oxygen saturation;
$A=\epsilon_4$;
$B=-\epsilon_2$;
$C=\epsilon_4-\epsilon_3$;
$D=\epsilon_1-\epsilon_2$;

$\epsilon_1$, $\epsilon_2$ are respectively an absorption rate of oxyhemoglobin to the red light and an absorption rate of deoxyhemoglobin to the red light; and $\epsilon_3$, $\epsilon_4$ are respectively an absorption rate of oxyhemoglobin to the infrared light and an absorption rate of deoxyhemoglobin to the infrared light;

wherein the at least one interval is divided into different confidence intervals according to different degrees of noise interference in a pulse fluctuation cycle, wherein a confidence value of one confidence interval with relatively high interference is less than that of another confidence interval with relatively low interference, wherein the total area integral of the signal for the light of the first wavelength comprises a sum of products of the area integral of the waveform of the signal for the light of the first wavelength in all the confidence intervals and the corresponding confidence, and wherein the total area integral of the signal for the light of the second wavelength comprises a sum of products of the area integral of the waveform of the signal for the light of the second wavelength in all the confidence intervals and the corresponding confidence.

* * * * *